US006326575B1

(12) United States Patent
Decaire et al.

(10) Patent No.: US 6,326,575 B1
(45) Date of Patent: Dec. 4, 2001

(54) NEEDLE INCINERATOR

(75) Inventors: Roy Decaire, St. Agatha; Petar Stancu, Brantford, both of (CA)

(73) Assignee: Spectrum Meditech Inc., Vancouver (CA)

( * ) Notice: Subject to any disclaimer, the term of this patent is extended or adjusted under 35 U.S.C. 154(b) by 0 days.

(21) Appl. No.: 09/563,588

(22) Filed: May 3, 2000

(51) Int. Cl.⁷ ................................................ B23H 1/00
(52) U.S. Cl. ............................................................. 219/68
(58) Field of Search ............................. 219/68; 110/250, 110/185, 141, 242; 206/365

(56) References Cited

U.S. PATENT DOCUMENTS

| | | | |
|---|---|---|---|
| 4,056,677 | * 11/1977 | Berk et al. . | |
| 4,096,375 | * 6/1978 | Fujino et al. . | |
| 4,388,722 | * 6/1983 | Tanimoto . | |
| 4,628,169 | 12/1986 | Ch'ing-Lung | 219/68 |
| 4,877,934 | 10/1989 | Spinello | 219/68 |
| 4,965,426 | 10/1990 | Colombo | 219/68 |
| 5,012,825 | * 5/1991 | Lindemann et al. . | |
| 5,075,529 | 12/1991 | Kudo | 219/10 |
| 5,281,789 | * 1/1994 | Merz et al. . | |
| 5,300,752 | 4/1994 | Elmerick et al. | 219/68 |
| 5,336,862 | 8/1994 | Yelvington | 219/68 |
| 5,468,928 | 11/1995 | Yelvington | 219/68 |
| 5,551,355 | * 9/1996 | Haines et al. . | |
| 5,710,404 | 1/1998 | Descent | 219/68 |
| 5,852,267 | 12/1998 | Yanobu | 219/68 |
| 5,868,709 | 2/1999 | Champion et al. | 604/110 |
| 5,877,469 | 3/1999 | Truesdale et al. | 219/68 |
| 6,148,742 | * 11/2000 | Constable et al. . | |

* cited by examiner

Primary Examiner—Tom Dunn
Assistant Examiner—Colleen Cooke
(74) Attorney, Agent, or Firm—Duane Morris & Heckscher LLP (57) ABSTRACT

The invention provides an incinerator adapted for disintegrating metal needles and lancets such as are used in the medical profession. An incinerator is provided that includes first and second electrodes, each having a contact edge spaced apart in an overlapping relationship to one another. The second electrode is rotated relative to the first electrode so as to define a tapered gap between the contact edges. A controlled power source is selectively interconnected to the first and second electrodes, with both being supported by a housing. The housing defines an opening adjacent to the electrodes for receiving metal, such as hypodermic needles, interveinous needles, lancets, etc., to be incinerated by the electrodes. In another embodiment of the invention, a residue collection drawer is slidably mounted within the housing adjacent to the electrodes so as to capture residue from the incineration. An electrode broom is movably mounted within the housing or the drawer, adjacent to the gap between the electrodes, so as to be movable against the contact edges thereby to remove a build-up of debris resulting from incineration.

24 Claims, 11 Drawing Sheets

NEEDLE INCINERATOR

FIELD OF THE INVENTION

The present invention generally relates to waste disposal devices, and more particularly to devices for disposing of needles associated with hypodermic syringes, lancets and the like.

BACKGROUND OF THE INVENTION

With the ever increasing need to prevent the spread of infectious diseases, there has been a growing emphasis on the safe handling and disposal of medical waste and particularly the needles utilized with hypodermic syringes. It is extremely important to protect medical personnel and others who are required to administer hypodermic injections from inadvertent or accidental "stick" injuries. This protection is also required by those who must dispose of medical waste by-products, including the hypodermic syringes and needles, from accidental "stick" injuries which can occur by the improper or accidental handling of such waste products.

In an effort to provide increased safety and prevent the spread of infectious disease, small incinerating devices have been developed in recent years which are specifically designed for destroying hypodermic syringe needles and the like. Most of these incinerating devices have been designed to be portable, and most operate on conventional 110 volt AC outlet current so that the units may be plugged into a conventional outlet. With these, and other, prior art devices, a needle may be destroyed immediately after its use by inserting the needle, while still attached to the hypodermic syringe, into the incinerating apparatus where heat or electricity is utilized to thermally neutralize biohazardous materials, and melt or disintegrate the needle. Some examples of such prior art incinerators are found in U.S. Pat. No. : 4,628,169 to Ching-Lung; U.S. Pat. No. 4,877,934 to Spinello: U.S. Pat. No. 4,965,426 to Colombo; U.S. Pat. No. 5,075,529 to Kudo; U.S. Pat. No. 5,091,621 to Butler; U.S. Pat. No. 5,138,125 to Salesses; U.S. Pat. No. 5,282,428 to Grevill, et al.; U.S. Pat. No. 5,288,964 to Walker, et al.; U.S. Pat. No. 5,300,752 to Elmerick, et al.; U.S. Pat. No. 5,336,862 and U.S. Pat. No. 5,468,928 to Yelvington; U.S. Pat. No. 5,551,355 to Haines et al.; U.S. Pat. No. 5,710,404 to Descent; U.S. Pat. No. 5,852,267 to Yanobu; U.S. Pat. No. 5,868,709 to Champion, et al.; and U.S. Pat. No. 5,877,469 to Truesdale, et al.

In many of these prior art incinerators, a pair of electrodes are engageable by a needle inserted into the incinerator housing. An electric arc is established through the needle, destroying the needle at temperatures of 1,000 degrees or higher, with the disintegration occurring substantially instantaneously. In some of the prior art incinerators, small fans are utilized to exhaust the by-products of combustion to the ambient atmosphere. To prevent the release of airborne contaminants or pathogens, which may remain in the gaseous material, some prior art devices utilize a filter element to filter the air before it is exhausted from the incinerator apparatus.

Unfortunately, prior art needle incinerating units have not met with acceptance by practitioners in the health care industry. For one thing, incinerating devices have not proven to be sufficiently capable of ensuring that all exhaust from the incinerating devices is purified to prevent smoke, toxins, trace metal contaminates, and airborne pathogens from being discharged to the atmosphere. many healthcare professionals do not want to place any type of incinerating apparatus within an enclosed area where people may be exposed to the exhaust.

Another disadvantage in prior art needle incinerators is the need to adjust the incinerator electrodes or contacts depending upon the type of needle which is to be destroyed. In many prior art incinerators, the electrodes for contacting the needle are fixed relative to one another or flexible relative to one another, so as to ensure contact with varying lengths of needles. In other prior art devices, gauges or dedicated entrance ports are utilized to accommodate different diameter needles. Also, prior art needle incinerators have not been adequately designed to cooperatively destroy needles associated with differing sizes of hypodermic syringes.

One other disadvantage associated with most prior art needle incinerators is the inability to clean electrodes without disassembly. In particular, after several needles have been disintegrated, a residue forms on the edges of the electrodes which degrades the performance of the disintegration process, and often provides a load on the battery that causes the battery to discharge. If left uncleaned, this buildup of combustion by-products, residue and debris may render the incinerator inoperative.

In view of the foregoing, there is a need to increase the operating performance, safety characteristics, self-cleaning treatment characteristics, and adaptability of needle incinerators.

SUMMARY OF THE INVENTION

The present invention provides an incinerator adapted for disintegrating metal needles and lancets such as are used in the medical profession. In one embodiment of the invention, an incinerator is provided that includes first and second electrodes, each having a contact edge spaced apart in an overlapping relationship to each other. The second electrode is rotated relative to the first electrode so as to define a tapered gap between the contact edges. A controlled power source is selectively interconnected to the first and second electrodes, with both being supported by a housing. The housing defines an opening adjacent to the electrodes for receiving metal, such as hypodermic needles, interveinous needles, lancets, etc., to be incinerated by the electrodes.

In another embodiment of the invention, a residue collection drawer is slidably mounted within the housing adjacent to the electrodes so as to capture residue from the incineration. An electrode broom is movably mounted within the housing or the drawer, adjacent to the gap between the electrodes so as to be movable against the contact edges thereby to remove a build-up of debris resulting from incineration.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein.

DETAILED DESCRIPTION OF THE PREFERRED EMBODIMENTS

This description of preferred embodiments is intended to be read in connection with the accompanying drawings, which are to be considered part of the entire written description of this invention. In the description, relative terms such as "horizonal," "vertical," "up," "down," "top" and "bottom", "back" and "front", as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

Figure 1:
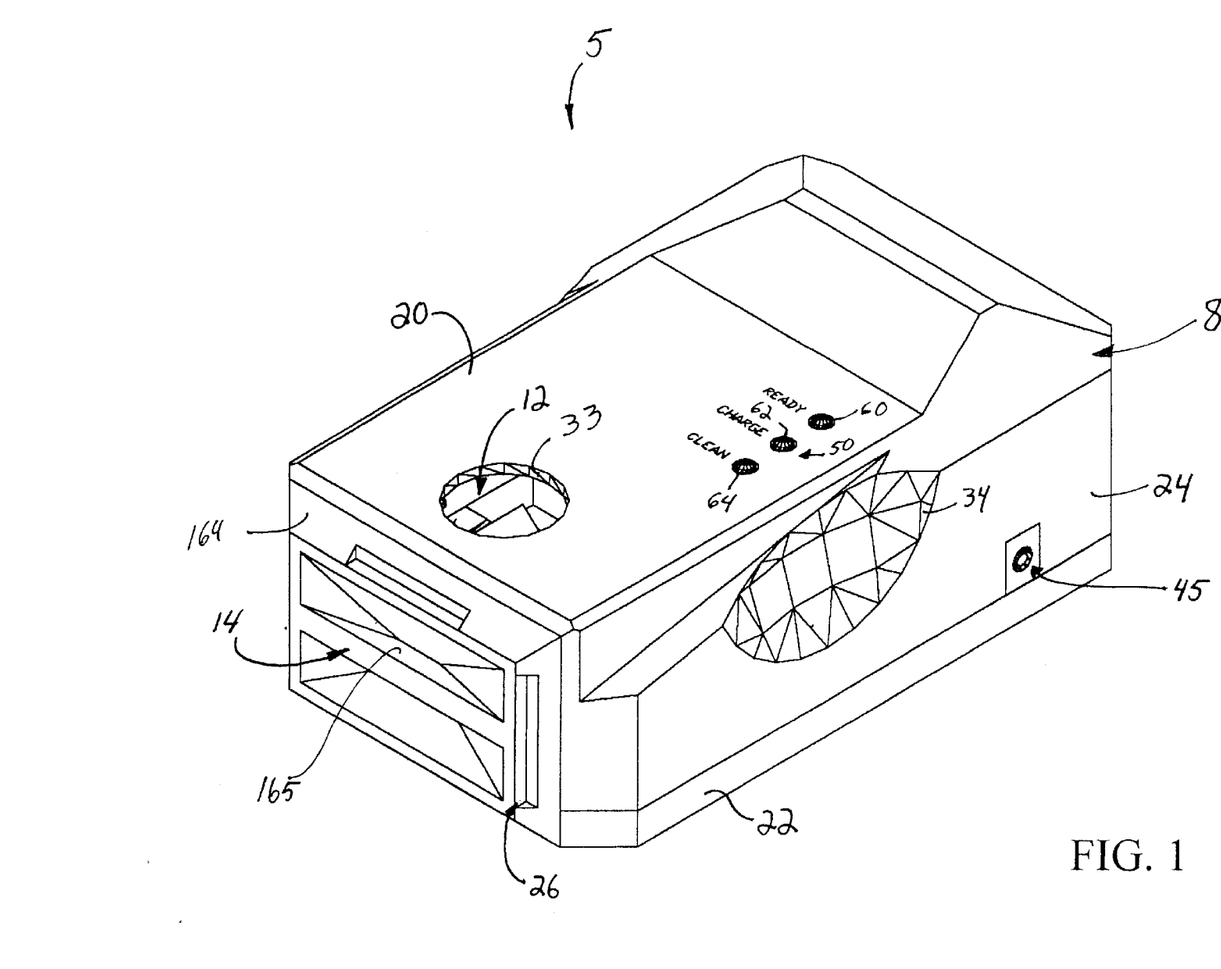
FIG. 1 is a perspective view of a needle incinerator formed in accordance with the invention.
Figure 2:
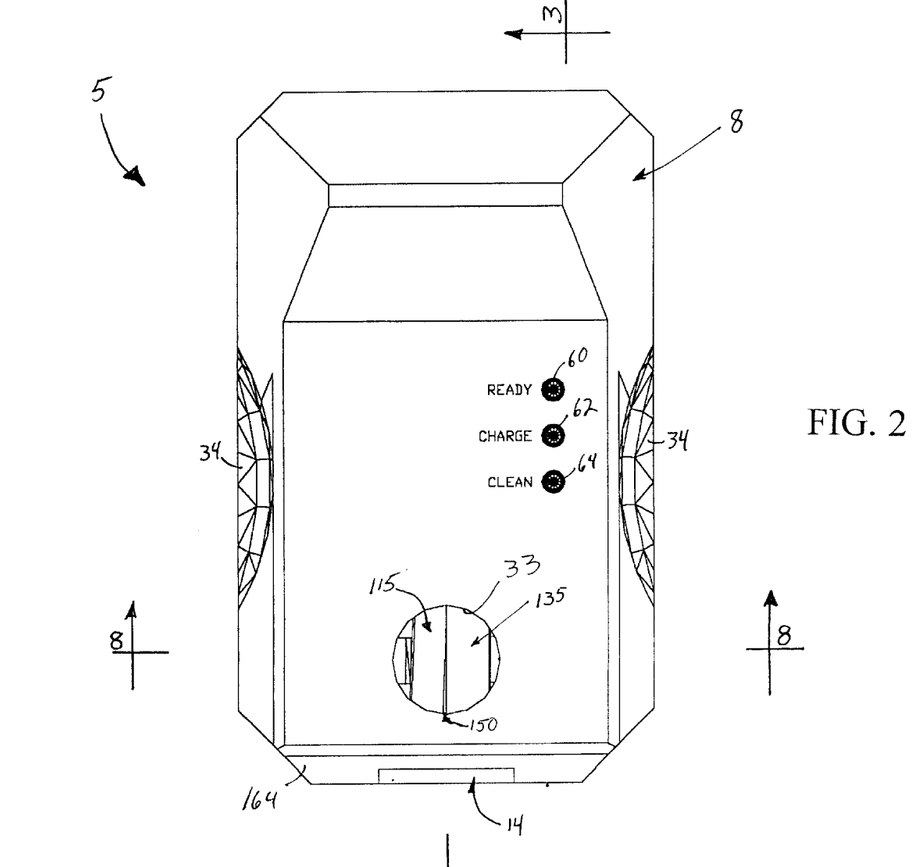
FIG. 2 is a top view of the needle incinerator shown in FIG. 1.
Figure 3:
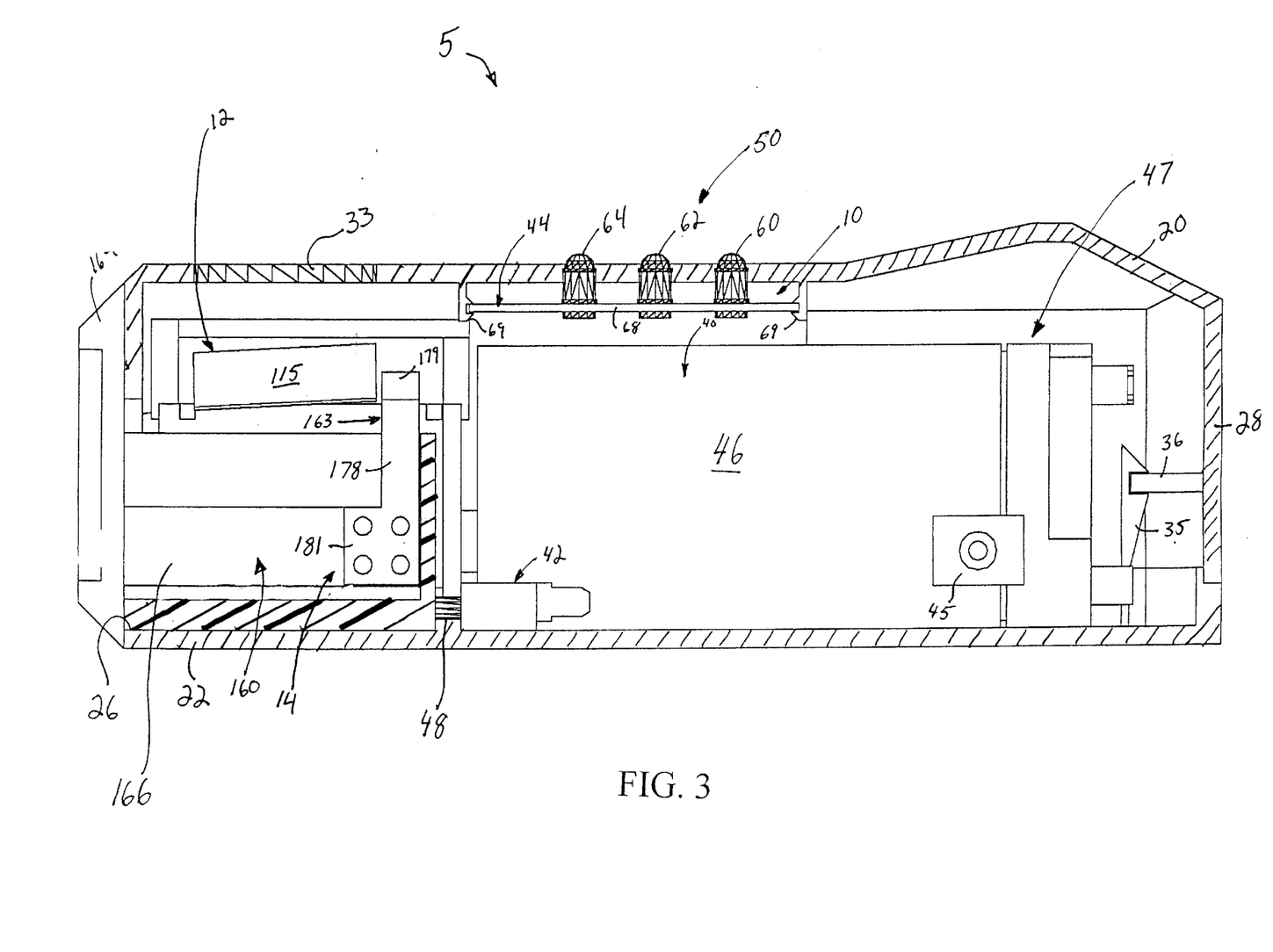
FIG. 3 is a cross-sectional view of the needle incinerator shown in FIGS. 1 and 2, as taken along lines 3—3 in FIG. 2.

Referring to FIGS. 1–3, a needle incinerator 5 formed in accordance with a preferred embodiment of the invention comprises a housing 8, a power and control assembly 10, an electrode assembly 12, and a cleaning assembly 14. More particularly, housing 8 includes a top wall 20, a bottom 22, sidewalls 24, a front opening 26, and a back wall 28 which are all arranged to define an interior void space or chamber 29 within housing 8. Housing 8 is preferably formed from a durable dielectric material, such as one of the well known engineering polymers, e.g., polyhalo-olefins, polyamides, polyolefins, polystyrenes, polyvinyls, polyacrylates, polymethacrylates, polypropylene, polyesters, polystyrenes, polydienes, polyoxides, polyamides and polysulfides and their blends, co-polymers and substituted derivatives thereof. Chamber 29 is sized and shaped to house power and control assembly 10, electrode assembly 12, and a cleaning assembly 14. Front opening 26 provides access for cleaning assembly 14 to be placed adjacent to a portion of electrode assembly 12, as will hereinafter be disclosed in further detail.

Figure 4:
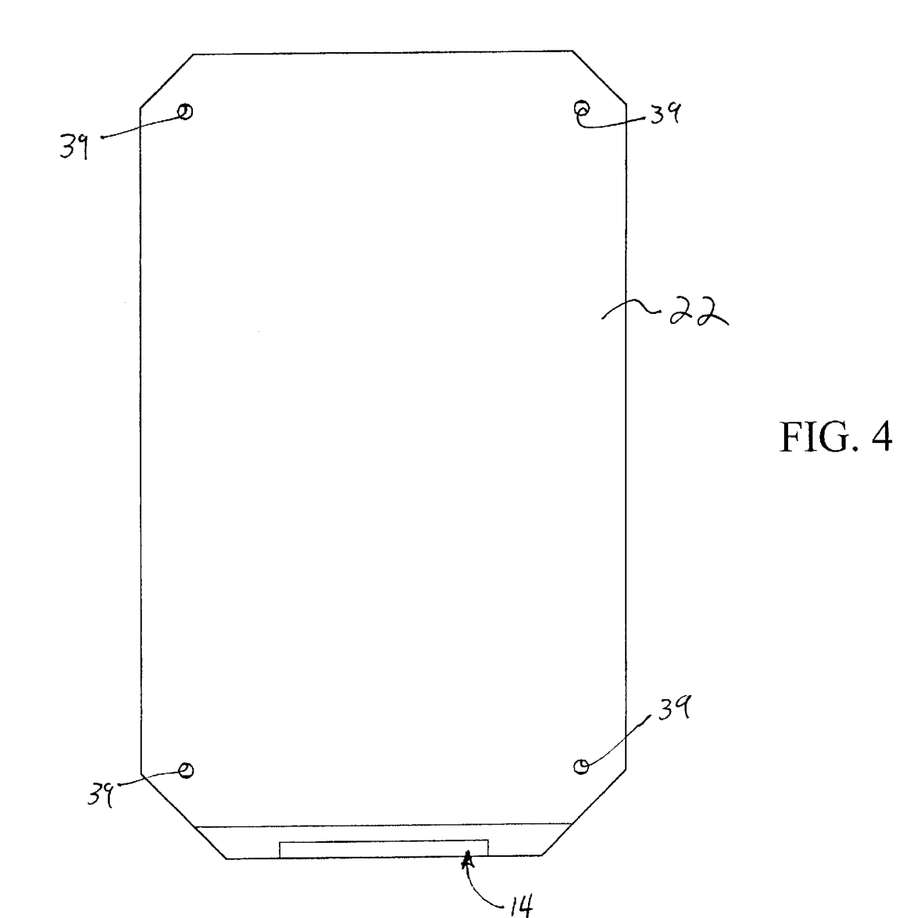
FIG. 4 is a plan view of the bottom wall of the needle incinerator shown in FIG. 1.
Figure 8:
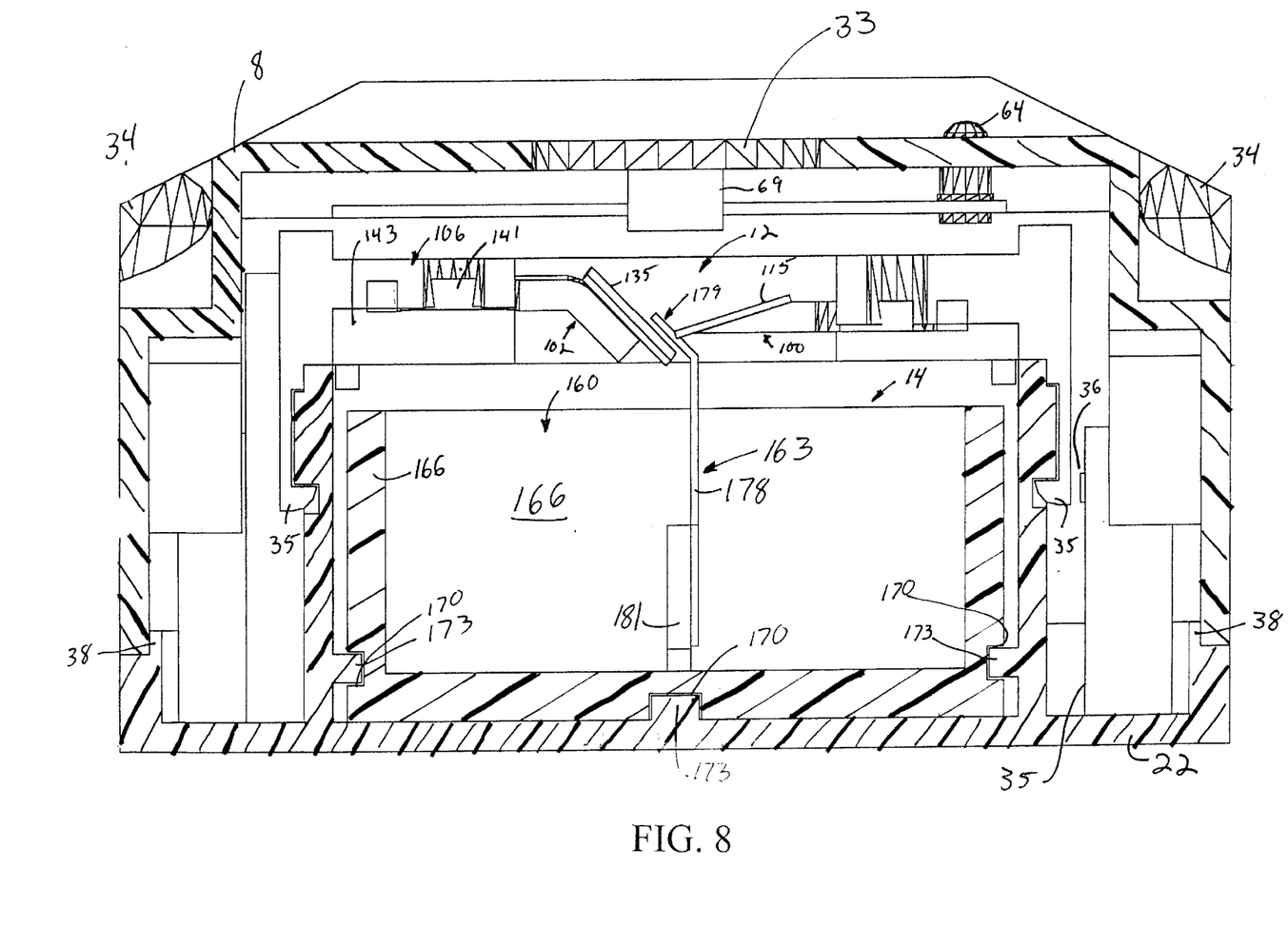
FIG. 8 is a cross-sectional view of the needle incinerator, as taken along lines 8—8 in FIG. 2.

Top wall 20 defines an opening 33 which provides access to electrode assembly 12. Opening 33 is the main aperture for inserting needles into needle incinerator 5 for incineration. Opening 33 is preferably circular, often with a radius of between 0.3 and 1.0 inches, and preferably about 0.6 inches. A semi-spherical indentation 34 is defined along an edge of housing 8 between top wall 20 and a sidewall 24 so that needle incinerator 5 can be carried with ease. Indentation 34 may be formed on both sides of housing 8 (FIGS. 2 and 8). Clips 35 are connected in the corners of bottom 22, and function to attach a top portion of housing 8 to bottom 22 (FIG. 4). Connection brackets 36 are positioned on the inner surface of sidewalls 24 to engage clips 35. An annular enclosure seal 38 is positioned around the perimeter of bottom 22. Enclosure seal 38 prevents dust and vapors from entering or exiting housing 8 through the interface of the housing top portion and bottom 22 when the housing fully assembled and operating.

Referring to FIG. 4, four holes 39 are defined in the corners of bottom 22. The primary function of holes 39 is to mount four rubber grommets (not shown) to act as feet for needle incinerator 5. A secondary function is to provide a port for the insertion of dowels (not shown) to unlock connection clips 35 from the connection brackets 36 and thereby release housing top portion and bottom 22.

Power and control assembly 10 is positioned within chamber 29 of housing 8, and includes a power source 40, a momentary action switch 42 and control electronics system 44. In a portable embodiment of the invention, direct current electrical energy is provided to electrode assembly 12 from a battery or batteries 46 located within a rear portion 47 of chamber 29. Alternatively, when alternating current is drawn from, e.g., conventional wall outlet and a plug arrangement, a transformer (not shown) is provided within rear portion 47 of chamber 29 to convert the alternating line current to direct current for use with electrode assembly 12. A power jack 45 is provided, and designed to sit flush with a sidewall 24 of housing 8. Power jack 45 accepts a plug (not shown) from a standard wall plug-in AC/DC adapter for recharging of battery 46. The choice of battery 46 or transformer is determined by the specific range of needles to be regularly incinerated with needle incinerator 5. For example, a needle incinerator 5 designed to incinerate 20 to 30 gauge needles may use a 6 Volt, 5 Amp-hour battery to accomplish the incineration. It will be understood that other ranges of gauges of needles may be incinerated with the present invention with a proper choice of battery capacity and electrode assembly.

Momentary action switch 42 preferably comprises a plunger-type actuator 48 to actuate the switch, and is electrically interconnected between power source 40, electrode assembly 12, and control electronics system 44. When plunger-type actuator 48 is fully depressed, momentary action switch 42 is closed, thereby allowing current to flow to electrode assembly 12. When plunger-type actuator 48 is fully extended, momentary action switch 42 is open, thereby stopping the flow of any current to electrode assembly 12. Operation of a portion of cleaning assembly 14 actuates momentary action switch 42, as will hereinafter be disclosed in further detail.

Control electronics system 44 includes an operations display 50, a display drive circuit 53, and a battery recharge protection circuit 56. More particularly, operations display 50 comprises at least three incinerator status indicators positioned on the surface of top wall 20. The at least three incinerator status indicators may include a "Ready" status indication light 60, a "Charge" status indication light 62, and a "Clean" status indication light 64. Status indication lights 60, 62, 64 are preferably light-emitting diodes (LED) each having a different color. For example, "Ready" status indication light 60, may be green to notify the user of needle incinerator 5 that the device is ready to incinerate a needle, and that there is sufficient power available from battery 46 to do so. "Charge" status indication light 62 may be a yellow (amber) LED to notify the user that battery 46 has a lower than needed charge and is in need of recharging. "Clean" status indication light 64 may be a red LED and, when on, notifies the user that there is a potentially harmful material lodged in an active portion of electrode assembly 12. During operation of needle incinerator 5, status indication lights 60, 62, 64 will often flicker or go out due to a drop in voltage from battery 46. When incineration is complete, one of the three lights will display to indicate to the user the status of needle incinerator 5. In the event that all three lights remain off after incineration, an under-voltage condition in battery 46 is indicated, at which time battery 46 can no longer be recharged and requires replacement.

Figure 5:
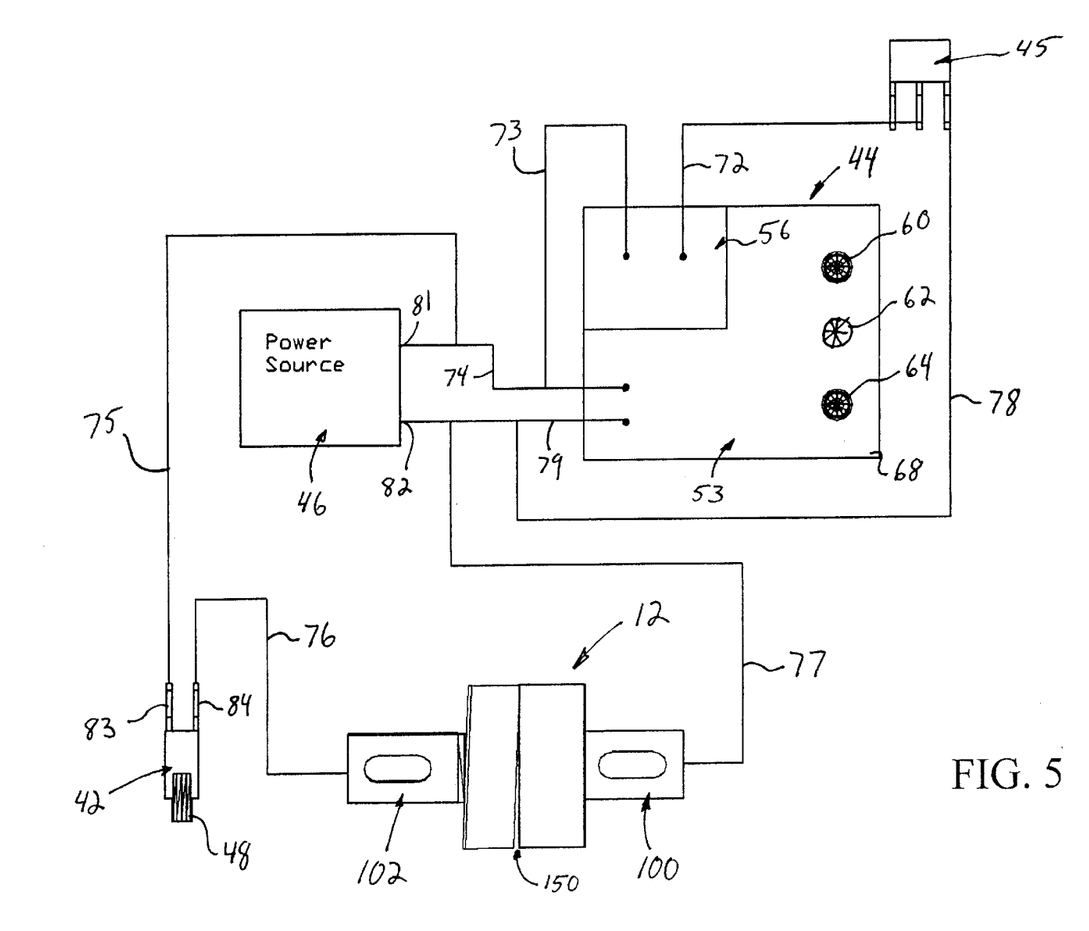
FIG. 5 is a schematic representation of one wiring and circuit arrangement used in connection with the present invention.

Referring to FIG. 5, main circuit board 68 contains the circuitry components that drive status indication lights 60, 62, 64 and the circuitry components that monitor and protect battery 46 during operation of needle incinerator 5 and recharging of battery 46. Circuit board connection clips 69 are used to attach main circuit board 68 to the inside of top wall 20 of housing 8. Main circuit board 68 is often split into two sections comprising display drive circuit 53 and battery monitoring and recharge protection circuit 56, and includes the appropriate passive and active electronic components and interconnection circuitry for driving status indication lights 60, 62, 64 and for monitoring the load placed upon battery 46 during operation and recharging, which devices and circuitry are conventional and well known to those of ordinary skill in the art.

For example, recharging lead wire 72 interconnects power jack 45 to battery recharge protection circuit 56. Recharging lead wire 73 interconnects battery recharge protection circuit 56 to positive terminal 83 of battery 46. LED drive circuit wire 74 interconnects battery 46 to LED drive circuit 53. Main lead wire 75 interconnects battery 46 to the positive terminal of momentary action switch 42. Incineration contact wires 76, 77 interconnect momentary action switch 42 and battery 46 to electrode assembly 12 so as to form a complete circuit. Recharging wire 78 interconnects battery 46 to power jack 45 to complete the circuit. LED drive wire 79 interconnects drive circuit 53 to battery 46 so as to complete the circuit. Battery terminal 81 is the connection site for the lead wire 75 which interconnects battery 46 to momentary action switch 42 so as to complete the circuit. Battery terminal 82 interconnects lead wire 77 to electrode assembly 12 to the power source so as to complete the circuit. Terminal 84 of momentary action switch 42 interconnects electrode assembly 12, via lead wire 76, to momentary action switch 42 so as to complete the circuit.

Referring to FIGS. 3, 5, and 6–8, electrode assembly 12 comprises a negative incineration contact 100, a positive incineration contact 102, and an incineration chamber cowl 106. More particularly, negative incineration contact 100 is formed from a highly conductive metal, such as copper or a copper alloy, and includes a substantially straight and elongate mounting arm 110 having a through hole 112 defined along its length and a needle engagement plate 115 positioned at one end. Through-hole 112 is sized to receive a portion of a mounting bolt or the like 116 for securely fastening negative incineration contact 100 to a bulkhead 118 positioned within a front portion of chamber 29 of housing 8. Needle engagement plate 115 comprises a substantially flat surface defining a needle contact edge 119, and is preferably formed from H&H 72/28 silver alloy, silver solder mounted to copper.

Figure 6:
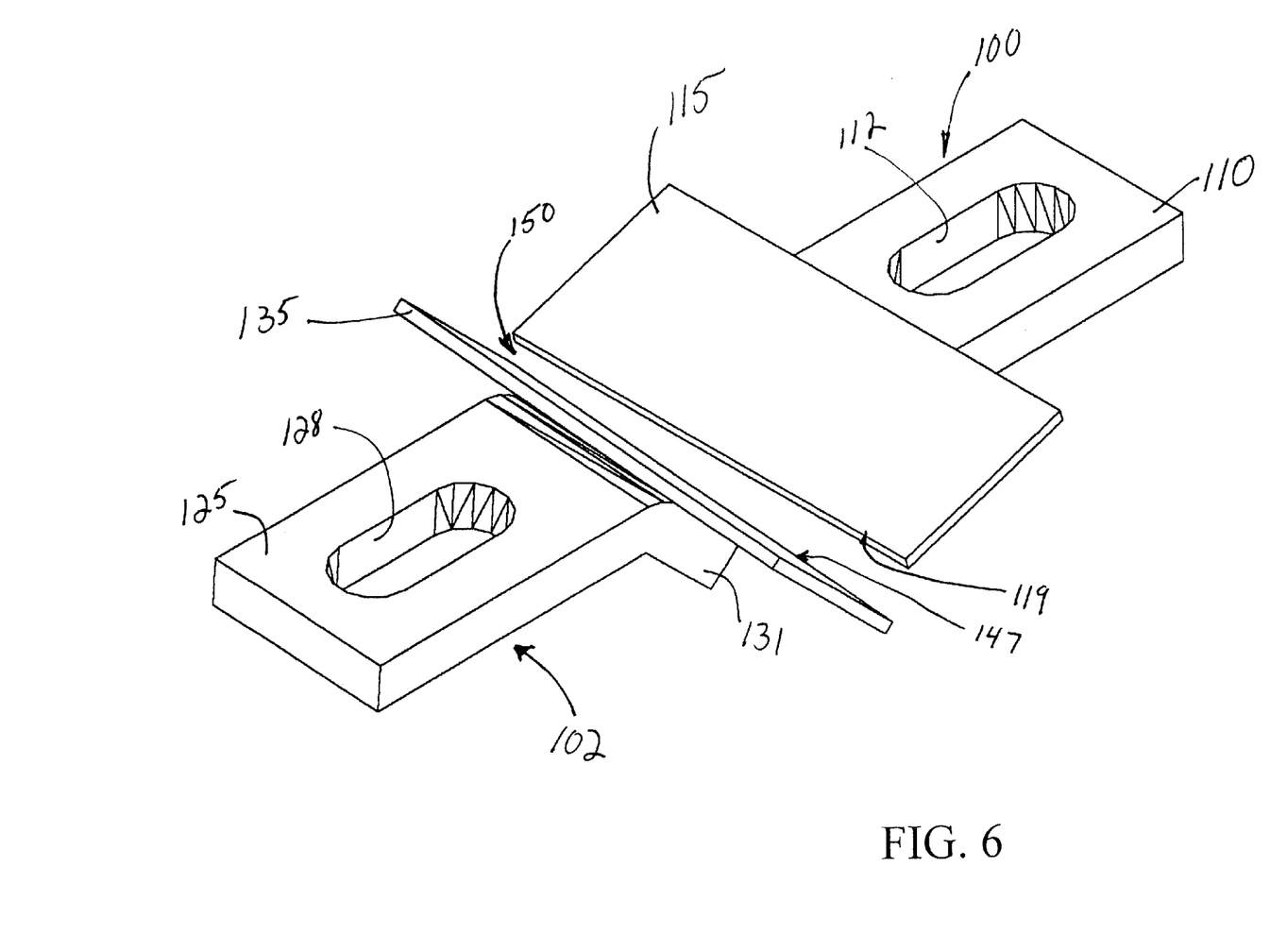
FIG. 6 is a perspective view of a negative incineration contact and a positive incineration contact that are used in connection with the electrode assembly of the needle incinerator, with surrounding structures removed for clarity of illustration.
Figure 7:
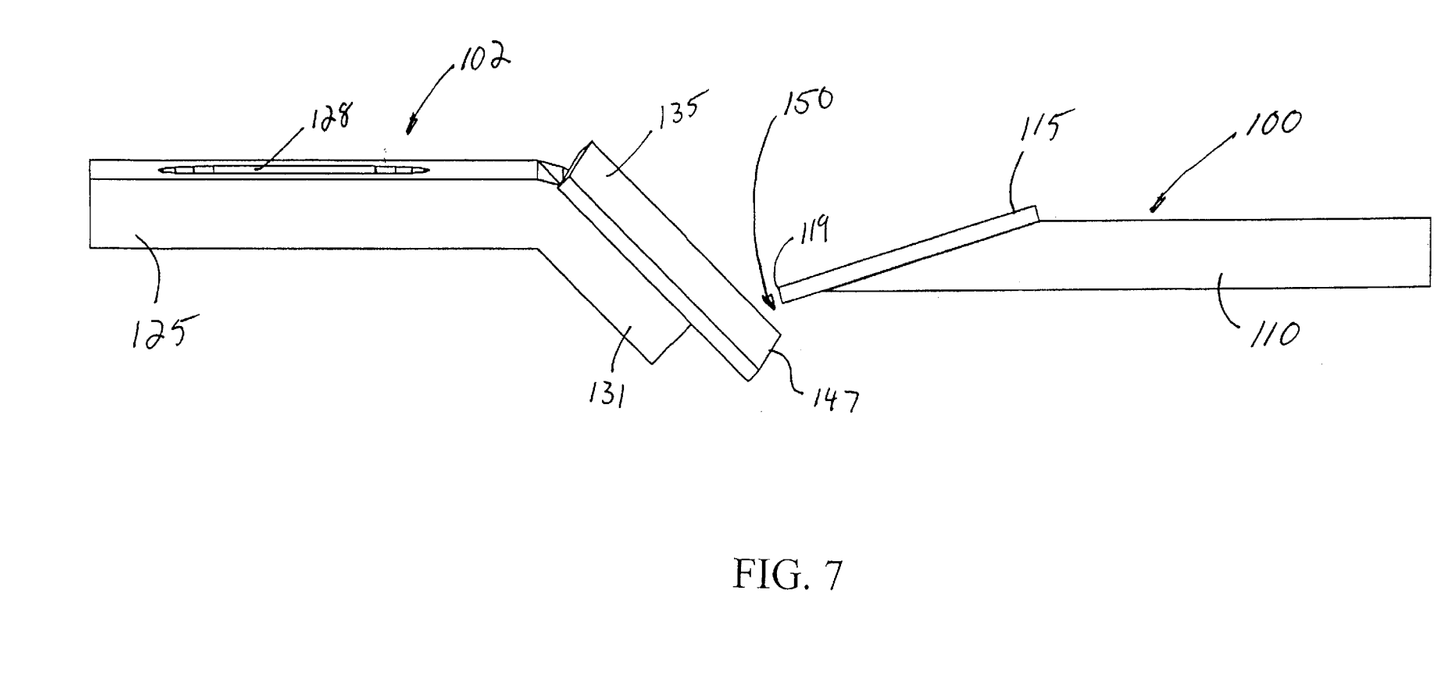
FIG. 7 is a side elevational view of the negative incineration contact and positive incineration contact shown in FIG. 6.

Negative incineration contact 100 is mounted to bulkhead 118 so that the longitudinal axis of mounting arm 110 is oriented substantially parallel to sidewalls 24 of housing 8, with needle contact edge 119 of needle engagement plate 115 disposed substantially under opening 33 in top wall 20 of housing 8. In this position, needle engagement plate 115 is oriented at an angle of between about 12 degrees to about 25 degrees, and preferably at an angle of about 17 degrees, relative to the longitudinal axis of mounting arm 110. This angled orientation of needle engagement plate 115 allows any needles entering electrode assembly 12, via opening 33, and encountering needle engagement plate 115 at an angle of incidence that causes the needle to stub on its surface, to be redirected toward needle contact edge 119 of needle engagement plate 115 and positive incineration contact 102 where the incineration of the needle is effected.

Positive incineration contact 102 is formed from a highly conductive metal, such as copper or a copper alloy, and includes a substantially straight and elongate mounting arm 125 having a through hole 128 defined along its length, a downwardly bent end portion 131, and a needle engagement plate 135 fastened to a top surface of end portion 131. Through hole 128 is sized to receive a portion of a mounting bolt or the like 141 for securely fastening positive incineration contact 102 to a bulkhead 143 positioned within a front portion of chamber 29 within housing 8. Needle engagement plate 135 comprises a substantially flat surface defining a needle contact edge 147, and is preferably formed from H&H 72/28 silver alloy, silver solder mounted to copper.

Positive incineration contact 102 is mounted to bulkhead 143 so that the longitudinal axis of mounting arm 125 is oriented substantially parallel to sidewalls 24 of housing 8, with needle contact edge 147 of needle engagement plate 135 disposed substantially under opening 33 in top wall 20 of housing 8. In this position, needle engagement plate 135 is oriented at an angle of between about 35 degrees to about 50 degrees, and preferably at an angle of about 45 degrees, relative to the longitudinal axis of mounting arm 125, and also rotationally oriented at an angle of between about 2 degrees and about 6 degrees, and preferably at an angle of about 4 degrees, relative to a vertical axis directed coaxially through opening 33 in top wall 20.

Advantageously, this combination of angular positions of positive incineration contact 102 provides a tapering gap 150 between needle contact edge 119 and needle contact edge 147. In other words, gap 150 defined between needle contact edge 119 and needle contact edge 147 is skewed such that it is narrower at one end (approximately between 0.018 and 0.024 inches) and wider at the other end (approximately between 0.028 and 0.035 inches). This feature provides a user with the capability to incinerate a large range of gauge sizes of needles, inasmuch as, larger gauge needles can be incinerated near the wider end of gap 150 and smaller gauge needles can be incinerated near narrower end of gap 150.

Incineration chamber cowl 106 is sized and shaped to enclose an upper portion of electrode assembly 12, adjacent to negative incineration contact 100 and positive incineration contact 102. Two or more clips 35 are used to connect incineration chamber cowl 106 to housing 8. Use of clips 35 allows for easy installation and service of electrode assembly 12.

Figure 9:
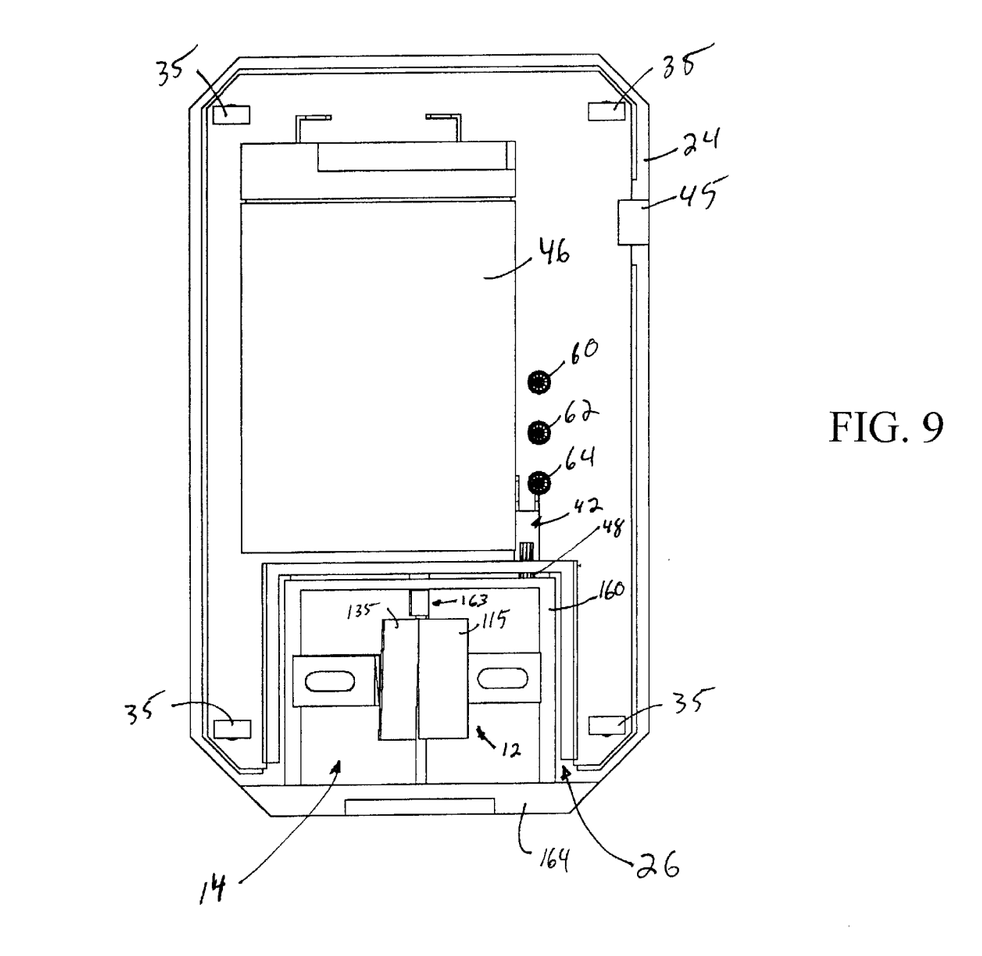
FIG. 9 is a top view of the needle incinerator shown in FIG. 1, but with a top portion of a housing removed for clarity of illustration.

Referring to FIGS. 3 and 8–9, cleaning assembly 14 includes a residue drawer 160 and a contact broom 163. Residue drawer 160 comprises four sidewalls 166 and a bottom 168 that together form an open receptacle that is sized and shaped to be slid through front opening 26 of housing 8, and beneath electrode assembly 12. A front wall 164 includes a handle 165 formed on an outer surface for grasping during the removal of residue drawer 160 from needle incinerator 5. The primary function of residue drawer 160 is to collect the waste residue formed as a result of the incineration of a plurality of needles, and provide for the easy disposal of that residue. The secondary function of residue drawer 160 is to support contact broom 163.

More particularly, each longitudinally oriented sidewall 166 and bottom 168 include a recessed channel 170 that are sized and shaped to receive corresponding guide rails 173 located on lower portions of bulkheads 118 and 143, and the inner surface of bottom 22 of housing 8. Recessed channels 170 and guide rails 173 cooperate when residue drawer 160 is slid into and out of front opening 26 to properly align residue drawer 160. This is especially important in order to orient contact broom 163 properly so as to clean incineration residue from needle contact edge 119 and needle contact edge 147. It should be noted that when residue drawer 160 is positioned fully within housing 8, a sidewall 166 engages and fully depresses plunger-type actuator 48 of momentary action switch 42, thereby closing momentary action switch 42, and allowing current to flow to electrode assembly 12 (FIG. 3).

Figure 10:
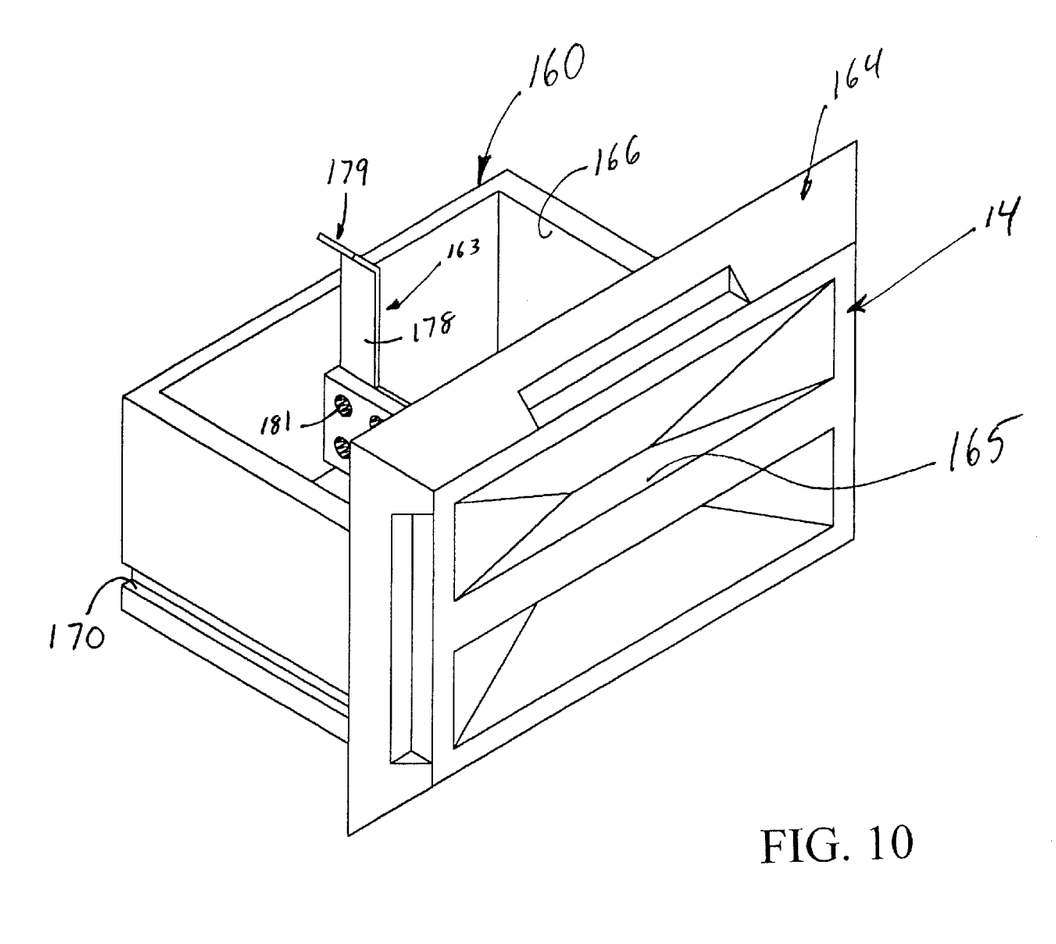
FIG. 10 is a perspective view of a cleaning assembly formed in accordance with the present invention, with the surrounding structures of the needle incinerator removed for clarity of illustration.
Figure 11:
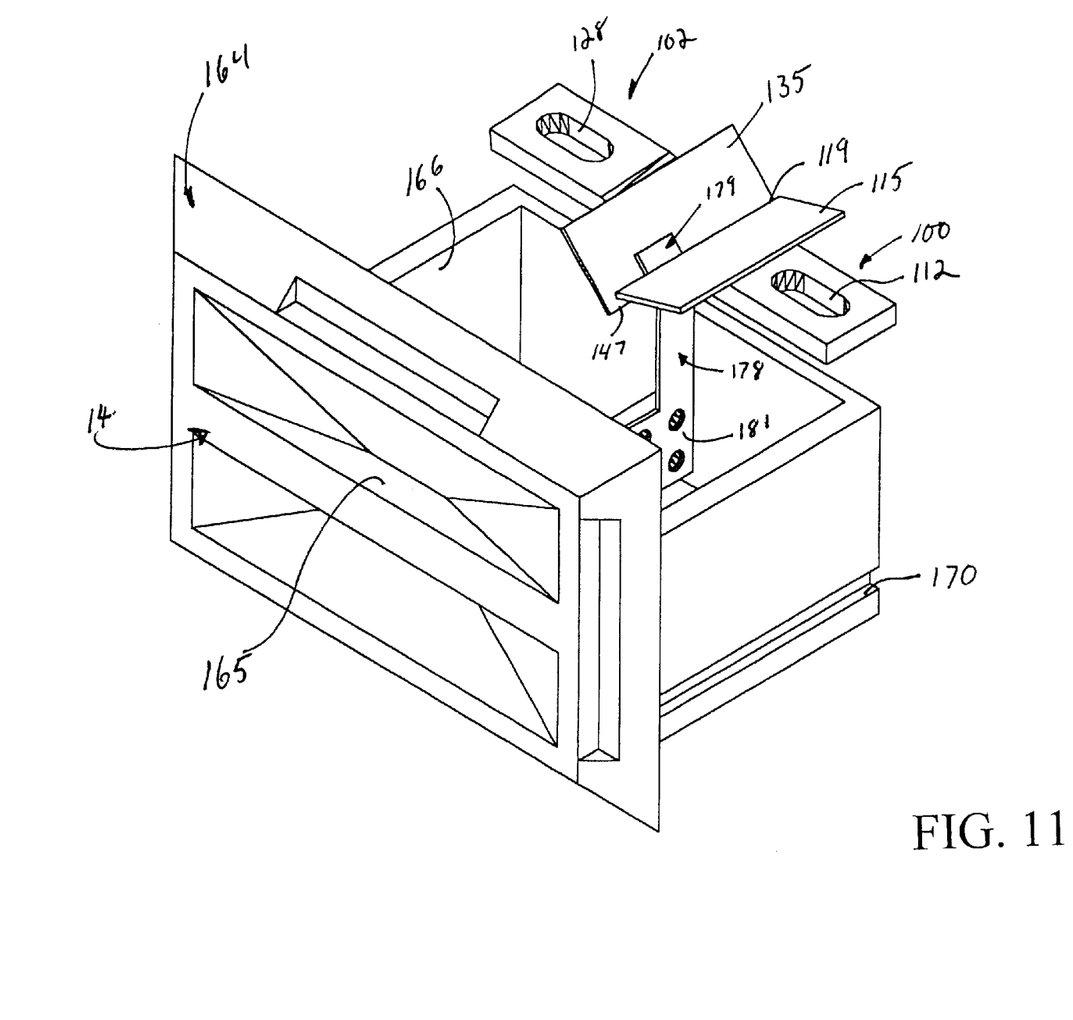
FIG. 11 is a perspective view of the cleaning assembly similar to FIG. 10, but including a negative incineration contact and a positive incineration contact that are used in connection with the electrode assembly of the needle incinerator, with the surrounding structures of the needle incinerator removed for clarity of illustration.

Contact broom 163 comprises an elongate rod 178 having an abrasive wire, plate, or bristle assembly 179 or any combination of the three fastened on one end. Bristle assembly 179 is sized and shaped to be slid within gap 150, from its narrowest end to its widest end, and back, so as to scrape and brush residue, debris, etc., from needle contact edges 119,147. Rod 178 is attached to a sidewall 166 of residue drawer 160 by means of clips or bolts 181 so as to project upwardly relative to bottom 168, with contact broom 163 positioned in spaced relation to residue drawer 160. In this way, when residue drawer 160 is slid into front opening 26 of housing 8, and fully positioned and properly aligned with electrode assembly 12, contact broom 163 is in coaxial aligned relation with gap 150 and spaced away from needle engagement plate 115 and needle engagement plate 135. This spacial relationship between contact broom 163 and the needle engagement plates is especially important in order to prevent an unwanted electrical short circuit through contact broom 163 during operation of needle incinerator 5.

When residue drawer 160 is removed from housing 8, contact broom 163 moves through gap 150 thereby sweeping needle contact edge 119 and needle contact edge 147, and thus removing any debris or residue left from an incineration. This is especially important as any metal residue or debris left engaging both needle engagement plate 115 and needle engagement plate 135 would quickly deplete any stored charge in battery 46, or potentially cause damage to the battery. In addition, the removal residue drawer 160 operates momentary action switch 42. More particularly, when residue drawer 160 is removed from housing 8, plunger-type actuator 48 is fully extended, and momentary action switch 42 is opened, thereby stopping the flow of any current to electrode assembly 12.

In operation, when battery monitoring and recharge protection circuit 56 senses a build up of debris (by monitoring an increase in load on battery 46 without incineration of a needle) status indication light 64 lights up to notify the user that needle engagement plate 115 and needle engagement plate 135 need to be cleaned. At this point, residue drawer 160 may be removed, and the collected debris and residue discarded. It should be noted that when residue drawer 160 is removed from housing 8, plunger-type actuator 48 is fully extended, opening the circuit so that no current can flow from the power source to electrode assembly 12. Also, when residue drawer 160 is removed, contact broom 163 sweeps through gap 150 removing any residue or debris left in the contacts after incineration of a needle. When residue drawer 160 is once again inserted completely into front opening 26, plunger-type actuator 48 is fully depressed, closing the circuit and allowing current to flow from battery 46 to electrode assembly 12. This process may be repeated as often as need be.

It is to be understood that the present invention is by no means limited only to the particular constructions herein disclosed and shown in the drawings, but also comprises any modifications or equivalents within the scope of the claims.

What is claimed is:

1. A metal incinerator comprising:
   first and second electrodes each having a contact edge spaced apart in an overlapping relationship to each other, wherein said second electrode is rotated relative to said first electrode so as to define a tapered gap between said contact edges;
   a controlled power source selectively interconnecting said first and second electrodes;
   a housing supporting said electrodes and said power source and having an opening for receiving metal to be incinerated by said electrodes and a residue collection drawer slidably mounted within said housing adjacent said first and second electrodes; and
   an electrode broom mounted to said residue collection drawer and adjacent said gap so as to be movable within said gap and against said contact edges thereby to remove a build-up of debris resulting from incineration of said metal.

2. An incinerator according to claim 1 wherein said first electrode comprises a substantially straight and elongate mounting arm having a through hole defined along its length and a needle engagement plate positioned at one end.

3. An incinerator according to claim 2 wherein said through-hole is sized to receive a portion of a mounting bolt for securely fastening said first electrode to a portion said housing.

4. An incinerator according to claim 3 wherein said needle engagement plate comprises a substantially flat surface defining said contact edge.

5. An incinerator according to claim 2 wherein said first electrode is mounted to a portion of said housing so that said mounting arm is oriented substantially parallel to a sidewall of said housing, with said contact edge disposed substantially under said opening.

6. An incinerator according to claim 2 wherein said first electrode is oriented at an angle of between about twelve degrees to about twenty-five degrees relative to said mounting arm.

7. An incinerator according to claim 2 wherein said first electrode is oriented at an angle of about seventeen degrees relative to said mounting arm.

8. An incinerator according to claim 1 wherein said second electrode comprises a substantially straight and elongate mounting arm having a through hole defined along its length, a bent end portion, and a needle engagement plate positioned on a top surface of said bent end.

9. An incinerator according to claim 8 wherein said through-hole is sized to receive a portion of a mounting bolt for securely fastening said second electrode to a portion said housing.

10. An incinerator according to claim 9 wherein said needle engagement plate comprises a substantially flat surface defining said contact edge.

11. An incinerator according to claim 8 wherein said second electrode is mounted to a portion of said housing so that said mounting arm is oriented substantially parallel to a sidewall of said housing, with said contact edge disposed substantially under said opening.

12. An incinerator according to claim 8 wherein said second electrode is oriented at an angle of between about thirty-five degrees to about fifty degrees relative to said mounting arm.

13. An incinerator according to claim 8 wherein said second electrode is oriented at an angle of about forty-five degrees relative to said mounting arm.

14. An incinerator according to claim 1 wherein said second electrode is rotated relative to said opening at an angle of between about two degrees and about six degrees.

15. An incinerator according to claim 1 wherein said second electrode is rotated relative to said first electrode at an angle of about four degrees relative to said opening.

16. A needle incinerator according to claim 1 comprising a momentary action switch electrically interconnected between said power source and said first and second electrodes and positioned within said housing so that when said residue collection drawer is positioned fully within said housing said momentary action switch is fully actuated thereby allowing power to flow to said first and second electrodes.

17. A metal incinerator comprising:
   first and second electrodes each having a contact edge spaced apart in an overlapping relationship to each other, wherein said second electrode is rotated relative to said first electrode so as to define a tapered gap between said contact edges;
   a controlled power source selectively interconnecting said first and second electrodes;
   a housing supporting said electrodes and said power source and defining an opening adjacent to said electrodes for receiving metal to be incinerated by said electrodes; and
   an electrode broom movably mounted within said housing adjacent said gap so as to be movable against said contact edges thereby to remove a build-up of debris resulting from incineration of said metal, wherein said electrode broom comprises an elongate rod having means for brushingly engaging said contact edges and a residue collection drawer slidably mounted within said housing adjacent said first and second electrodes wherein said rod is fastened to a sidewall of said residue drawer.

18. A metal incinerator according to claim 17 wherein said electrode broom comprises at least one of an abrasive wire, a plate, and a bristle assembly fastened to an end adjacent to said contact edges.

19. A metal incinerator according to claim 17 wherein said electrode broom is sized and shaped to be slid within said tapering gap, from a narrowest end to a widest end, and back, so as to scrape and brush residue from said contact edges.

20. A metal incinerator according to claim 17 wherein said rod projects upwardly relative to said bottom of said residue collection drawer, with said electrode broom so that when said residue collection drawer is slid into said opening of said housing, said electrode broom is in coaxial aligned relation with said gap and spaced away from said first and said second electrodes.

21. A needle incinerator comprising:
   a housing having an opening therein for receiving a needle,
   needle destruction means disposed within said housing adjacent said opening for contacting and destroying said needle;
   a residue collection drawer slidably mounted within said housing adjacent said needle destruction means; and
   a momentary action switch electrically interconnected between said power source and said first and second electrodes and positioned within said housing so that when said residue collection drawer is positioned fully within said housing said momentary action switch is fully actuated thereby allowing power to flow to said first and second electrodes.

22. A needle incinerator according to claim 21 wherein said residue collection drawer comprises four sidewalls and a bottom that together form an open receptacle that is sized and shaped to be slid through said opening of said housing and beneath said needle destruction means so as to collect the waste residue formed as a result of incineration of a plurality of needles.

23. A needle incinerator according to claim 22 wherein two of said sidewalls are oriented longitudinally relative to said bottom and include a recessed channel that is sized and shaped to receive corresponding guide rail located on a lower portion of said housing wherein said recessed channels and guide rails cooperate when said residue drawer is slid into and out of said opening so to properly align said residue drawer within said housing.

24. A needle incinerator according to claim 21 comprising a power source adapted for providing power to said needle destruction means and a momentary action switch electrically interconnected between said power source and said needle destruction means and positioned within said housing so that when said residue collection drawer is positioned fully within said housing said momentary action switch is fully actuated thereby allowing power to flow to said needle destruction means.

* * * * *